United States Patent [19]

Myers

[11] 4,289,919

[45] Sep. 15, 1981

[54] CATALYTIC ISOMERIZATION OF AN INTERNAL DOUBLE BOND ALIPHATIC MONO-OLEFIN TO PRODUCE TERMINAL BOND OLEFIN

[75] Inventor: John W. Myers, Bartlesville, Okla.

[73] Assignee: Phillips Petroleum Company, Bartlesville, Okla.

[21] Appl. No.: 186,861

[22] Filed: Sep. 12, 1980

Related U.S. Application Data

[63] Continuation-in-part of Ser. No. 41,589, May 23, 1979, abandoned.

[51] Int. Cl.$^3$ .............................................. C07C 5/25
[52] U.S. Cl. ............................... 585/664; 252/455 R; 252/471
[58] Field of Search ................... 585/664; 252/455 R, 252/471

[56] References Cited

U.S. PATENT DOCUMENTS

| | | | |
|---|---|---|---|
| 2,304,154 | 12/1942 | Doran | 585/653 |
| 2,818,451 | 12/1957 | Myers | 585/480 |
| 3,501,395 | 3/1970 | Miale | 585/664 |
| 3,509,041 | 4/1970 | Miale | 585/664 |

OTHER PUBLICATIONS

R. H. Ewell et al., J. of Am. Chem. Soc., vol. 63, No. 12, pp. 3460–3466, Dec. 17, 1941.
D. S. MacIver et al., J. Catalysis, 3, pp. 502–511, 1964.
Alumina Properties, Aluminum Co. of America, pp. 52–61.

*Primary Examiner*—Jacqueline V. Howard

[57] ABSTRACT

An aliphatic mono-olefin e.g. butene-2 is isomerized in the presence of a catalyst comprising essentially a small amount of a manganese oxide supported on an activated alumina to produce the corresponding terminal olefin selectively.

7 Claims, No Drawings

CATALYTIC ISOMERIZATION OF AN INTERNAL DOUBLE BOND ALIPHATIC MONO-OLEFIN TO PRODUCE TERMINAL BOND OLEFIN

This is a continuation-in-part of Ser. No. 41,589 filed May 23, 1979, now abandoned.

BRIEF SUMMARY OF THE INVENTION

An aliphatic mono-olefin having an internal double bond is isomerized, selectively, to give improved yields of the corresponding terminal olefin by subjecting the mono-olefin under isomerization conditions of a small catalytic amount of a manganese oxide supported on an activated alumina.

DETAILED DESCRIPTION

This invention relates to the selective isomerization of an aliphatic mono-olefin. More particularly, it relates to the selective isomerization of an aliphatic mono-olefin having an internal double bond to produce and to improve the yield of the corresponding terminal olefin. In a further aspect of the invention, it relates to a catalytic isomerization process.

In one of its concepts, the invention provides a process for the isomerization of an aliphatic mono-olefin having an internal double bond to produce, selectively, and to improve yield of a corresponding terminal olefin which comprises subjecting said mono-olefin under isomerization conditions including an elevated temperature to a catalyst comprising essentially a small effective amount of a manganese oxide supported on an activated alumina.

In another of its concepts, the invention provides an isomerization process as described in which the catalyst used is prepared by steps comprising adding a solution of a manganese compound to the selected alumina and then heating to convert the compound to oxide. In a further concept of the invention, still, there is provided a process wherein mono-olefins having from four to 20 carbon atoms inclusive are isomerized selectively to produce good yields of 1-or terminal double bond containing olefins.

Terminal olefins, also called 1-olefins or alpha-olefins, are useful as reactants for a number of commercially important processes, such as hydroformylation, sulfation, alkylation, and acid oligomerization. In these processes they are more reactive than internal olefins. The homologous series of 1-olefins can be prepared by the thermal cracking of paraffinic hydrocarbons. However, olefins produced by catalytic cracking will generally have close to thermodynamic equilibrium composition, determined by the cracking temperature, for the mixture of normal and branched isomers. These isomers are frequently not easily separated. When the normal and branched isomers can be separated from each other, as with butenes, then the normal olefins can be treated by the catalyst of this invention to provide a fraction that is enriched in 1-olefins.

Formation of 1-olefins is favored by the use of high temperatures, i.e., the concentration of 1-olefins in an equilibrium mixture of normal olefins always increases with increasing temperature. Elevated temperatures are known, unfortunately, to make skeletal isomerization of normal olefins more probable and therefore a problem, in attempts to maximize the yields of 1-olefins which are limited by the temperature at which skeletal isomerization becomes excessive.

In the Journal of the American Chemical Society, Volume 63, pages 3460–3466 (1941), in an article entitled Isomerization Equilibrium among the Branched Chain Pentenes by R. H. Ewell and P. E. Hardy, there are reported the results of eighteen runs in which isomerization of n-pentenes was investigated. These are listed in Table III of the article. Data were obtained in various experiments which were conducted by the authors. Comparison of runs at approximately the same temperatures and same times with and without manganese oxide in the catalyst shows that the added manganese oxide apparently did not improve the reaction. Indeed, comparing run 51 with runs 46 and 44 it would appear that the addition of the manganese oxide, even though the runs were at a somewhat higher temperature, gave a somewhat lower yield of 1-pentene. The article states, on page 3465, at foot of column 1, that ". . . most of the catalysts produced approximately the same amount of isomerization of 2-pentene, . . . " There is no finding of anything of significance for the runs which included the manganese oxide as against those which did not do so.

It is especially noted that the article on page 3462, in column 2, prepared a catalyst which contained 25 percent of manganese oxide.

I have now discovered that alumina containing a considerably smaller amount of manganese oxide, as herein further described, will effectively cause shifting of the double bond of the aliphatic mono-olefin to a terminal or 1- position.

It is an object of this invention to provide a process for the shifting of an internal double bond in an aliphatic mono-olefin hydrocarbon to terminal position. It is another object of this invention to provide a catalytic process for shifting an internal double bond in an aliphatic mono-olefin to 1- or terminal position. It is a further object of the invention to provide a catalytic process for the selective isomerization of shifting of an internal unsaturation or double bond in an aliphatic mono-olefin to a terminal or 1-position. It is an especial object of the invention to provide a process in which an amount of manganese oxide is employed which is effective to provide selective shifting of the internal double bond of the mono-olefin to a 1- position.

Other aspects, concepts, objects and the several advantages of the invention are apparent from a study of this disclosure and the appended claims.

According to the present invention, the double bond of an aliphatic mono-olefin is shifted from an internal position to a terminal position by contacting said mono-olefin under isomerization conditions with a catalyst essentially comprising a small amount of a manganese oxide upon an activated alumina.

By "activated alumina" as employed herein there is intended to include those manufactured aluminas the properties of which are like unto those given in "Alumina Properties, Technical Paper No. 10, Second Revision, Alumina Company of America, Pittsburgh, Pa. (1960) pages 52–61, authored by J. W. Newson et al". The disclosure of the reference work is incorporated herein by reference.

The catalyst of this invention comprises a catalytic alumina with a small amount of manganese oxide. The alumina is commonly known as activated alumina; it has a surface area generally greater than 50 m$^2$/g and may be gamma or eta alumina. The manganese can be incorporated into the alumina by coprecipitation, but a now preferred procedure is to add the manganese by impregnation with a solution—either organic or aqueous—of a suitable compound to preformed particles of activated alumina. In this manner the manganese is deposited at or near the surface of the catalyst and can modify the alumina economically and efficiently.

Manganese compounds that are suitable to add to the alumina are those which, when heated sufficiently, are decomposed to manganese oxide. The exact composition of the manganese oxide that is produced in this way is not known—it may be MnO, $Mn_2O_3$, and/or $MnO_2$, or even other oxides of manganese. Hence the valence of manganese being added to alumina is unimportant. Suitable compounds are manganese nitrate, and manganese salts of organic acids such as manganese acetate, manganese oxalate, manganese citrate, manganese tartrate, manganese benzoate, and the like. Much less desirable and frequently objectionable are halogen-containing salts of manganese. These latter compounds can react with alumina to form, e.g., aluminum halide, that can destroy the selectivity of the catalyst.

The amount of manganese to add to the alumina is small and can be from about 0.2 to about 8 weight percent, expressed as the element and based on the weight of alumina prior to treatment. Preferably the amount of manganese will be from about 0.4 to about 4 percent—on the same basis.

It is within the scope of this invention to impregnate the support and to convert to the catalyst while cycling a mono-olefin charge stock, or other hydrocarbon, in contact with the catalyst. In such event, the choice of manganese containing compound should include at least one compound containing oxygen ultimately to have the desired amount of manganese oxide on the support.

Aliphatic mono-olefins having more than three carbon atoms are amenable to treatment by the catalyst of this invention. This includes branched as well as normal compounds. With both, the equilibrium concentration of the 1-olefin isomer increases with increasing temperature. In general, olefins being treated will have between four and 20 carbon atoms.

Such olefins include pentene-2, 2-methylbutene-2, hexene-2, hexene-3, 3-methylpentene-2, heptene-2, heptene-3, octene-2, octene-3, octene-4, etc.

Especially preferred as feedstock to be treated with this catalyst are the isomeric n-butenes.

The temperature at which isomerization is effected with this catalyst is 260°–649° C. (500°–1200° F.). Preferably the temperature will be in the range of 316°–593° C. (600°–1100° F.).

Reaction pressure is not critically important. It can be subatmospheric, and preferably will not exceed about 200 psig to avoid bi-molecular condensation reactions that ultimately lead to excessive coke formation on the catalyst.

Contact time of reactants on the catalyst, expressed as liquid hourly space velocity (LHSV), can range between about 0.5–50. Preferably it will be between about one and 30.

EXAMPLE

The following example will serve to illustrate this invention.

Catalyst preparation: To 49.0 g (70 cc) of eta alumina (1/16 inch extrudate) that had been previously dried at 370° C. was added 29 cc of aqueous solution containing 1.23 g manganous nitrate (0.377 g Mn). After mixing well by stirring the mixture was dried at 100° C. in a forced draft oven for about 24 hours, then heated in air in a muffle furnace at 370° C. for two hours. This catalyst contained 0.76 weight percent manganese as oxide.

This manganese-treated alumina and the untreated eta alumina were tested for activity to isomerize butenes. Two cc of catalyst (ground and sieved to 20/28 mesh) was packed in a 7 mm i.d. quartz reactor having a 3 mm o.d. thermowell centered axially in the 13-cm long catalyst bed. Pure butene-2 feed mixed with nitrogen (mole ratio nitrogen/butene=4) passed down flow through the reactor at a butene rate of 2 LHSV. Samples of reaction product were taken after 30 minutes on stream at 454°, 482°, and 510° C. (850°, 900°, and 950° F.) and analyzed by GLC on a 25 ft.×⅛ inch o.d. column of dimethylsulfolane on 60/80 mesh Chromosorb P, at ambient temperature, with helium carrier. Results of these tests are tabulated in Table I.

TABLE I

| Catalyst | Eta Alumina | | | Eta Alumina + 0.76% Mn (as oxide) | | |
|---|---|---|---|---|---|---|
| Temp., °C. | 454 | 482 | 510 | 454 | 482 | 510 |
| Ethylene | ND* | 0.04 | 0.17 | ND | ND | 0.12 |
| Propylene | 0.67 | 0.87 | 1.44 | 0.03 | 0.06 | 0.16 |
| n-Butane | 0.16 | 0.19 | 0.28 | 0.10 | 0.12 | 0.15 |
| Butene-1 | 21.27 | 21.92 | 23.09 | 26.52 | 27.99 | 29.61 |
| iso-Butene | 16.01 | 17.28 | 16.22 | ND | ND | ND |
| t-Butene-2 | 35.45 | 34.03 | 33.28 | 41.90 | 41.12 | 39.85 |
| c-Butene-2 | 26.03 | 25.29 | 25.07 | 30.93 | 30.68 | 30.07 |
| Butadiene-1,3 | ND | ND | 0.14 | ND | ND | ND |
| Polymer | 0.41 | 0.38 | 0.31 | 0.53 | 0.04 | 0.04 |

*None detected

With pure butene-2 as the feed, these runs showed that on both catalysts the yield of butene-1 increased with increasing temperature. These yields are significantly greater, however, on the catalyst that had been treated with manganese because none of the n-butenes was converted to iso-butene. In contrast, the untreated eta alumina made about 16–18 percent isobutene. In addition it produced more propylene than the treated catalyst did, which is suggestive of cracking activity and definitely lowers the selectivity of the isomerization process. The generally higher yields of polymer, and the production of butadiene at 510° C., also illustrate undesirable properties of eta alumina that are diminished by treatment with manganese.

Reasonable variation and modification are possible within the scope of the foregoing disclosure and the appended claims to the invention the essence of which is that a mono-olefin, as described, having an internal double bond is isomerized to shift the double bond to the 1-or terminal position employing for this purpose under isomerization conditions a small amount of manganese oxide supported on activated alumina, as described.

I claim:

1. A process for the isomerization of an aliphatic mono-olefin hydrocarbon feed to shift an internal double bond therein to produce a corresponding terminal olefin which comprises subjecting said mono-olefin hydrocarbon under isomerization conditions which include a temperature in the approximate range of from about 500° to about 1200° F. to the action of a catalyst comprising a small amount of a manganese oxide supported on an activated alumina, said oxide being present in the approximate range of from about 0.2 to about 8 wt. %, expressed as the element based on the weight of the activated alumina.

2. A process according to claim 1 wherein the catalyst used is prepared by steps comprising adding a solution of a manganese compound to the alumina and then heating to convert the compound to oxide.

3. A process according to claim 2 wherein said oxide has been added to said activated alumina as a compound of manganese by essentially one of a coprecipitation and an impregnation method.

4. A process according to claim 1 wherein the monoolefin is at least one having from 4 to 20, inclusive, carbon atoms.

5. A process according to claim 4 wherein the monoolefins are inclusive of a substantial proportion of butene-2.

6. A process according to claim 3 wherein the monoolefin is a mixture which contains a substantial proportion of butene-2, the catalyst is prepared using for support at least one of gamma and eta alumina and the manganese compound is converted to oxide.

7. A process according to claim 1 wherein said monoolefin hydrocarbon feed contains a substantial proportion of butene-2 thereby producing a substantial proportion of butene-1 and wherein the catalyst is manganese oxide supported on an activated alumina having the properties of at least one of gamma and eta alumina and said oxide has been added as a compound of manganese to said activated alumina by essentially one of a coprecipitation and an impregnation method and a composition thus obtained has been heated to convert said compound in said composition to said oxide.

* * * * *